(12) United States Patent
Horvath et al.

(10) Patent No.: US 6,531,490 B1
(45) Date of Patent: Mar. 11, 2003

(54) PRODUCTION OF AGGLOMERATES OF INOGATRAN AND THE COMPOUND INOGATRAN ANHYDRATE

(75) Inventors: Karol Horvath, Södertälje (SE); Bo Lindqvist, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/646,440

(22) PCT Filed: Jun. 6, 2000

(86) PCT No.: PCT/SE00/01165

§ 371 (c)(1),
(2), (4) Date: Sep. 18, 2000

(87) PCT Pub. No.: WO00/76504

PCT Pub. Date: Dec. 21, 2000

(30) Foreign Application Priority Data

Jun. 10, 1999 (SE) .............................................. 9902202

(51) Int. Cl.[7] .......................... A61K 31/445; A61K 9/14
(52) U.S. Cl. ........................................ 514/330; 424/489
(58) Field of Search ........................... 424/489; 514/330

(56) References Cited

FOREIGN PATENT DOCUMENTS

| JP | 58143832 | 8/1983 |
|----|----------|--------|
| JP | 01279869 | 11/1989 |
| JP | 04077422 | 3/1992 |
| WO | 9311152 | 6/1993 |
| WO | 9739770 | 10/1997 |
| WO | 9749681 | 12/1997 |
| WO | 9816252 | 4/1998 |

*Primary Examiner*—Thurman K. Page
*Assistant Examiner*—Amy E Pulliam
(74) *Attorney, Agent, or Firm*—White & Case LLP

(57) ABSTRACT

A process for producing spherical agglomerates of inogatran having a narrow size distribution, and the compound inogatran anhydrate.

10 Claims, No Drawings

PRODUCTION OF AGGLOMERATES OF INOGATRAN AND THE COMPOUND INOGATRAN ANHYDRATE

TECHNICAL FIELD

The present invention relates to a process for producing compact, spherical agglomerates of inogatran having a narrow size distribution and to inogatran anhydrate.

Inogatran is a low molecular weight thrombin inhibitor exhibiting oral bioavailability, low variability and limited food interaction. The full chemical name of inogatran is: glycine, N-[2-[2-[[[3-[(aminoiminomethyl)amino]propyl] amino]carbonyl]-1-piperidinyl]-1-(cyclohexylmethyl)-2-oxoethyl]-[2R-[2S]]-and it is disclosed in WO93/11152 (Example 67).

Inogatran i s a slowly crystallising substance showing four polymorphs, of which the one produced by the process of this invention is anhydrous, not hygroscopic and stable.

BACKGROUND ART

A crystalline active drug substance is normally subjected to several processing steps before it is in a form suitable for administration to a human. Such steps are, for example, dry mixing with a filler and a disintegrant, and subsequently adding a binder to form granules; and drying, milling and/or mixing the granules with one or more further additives before a coating is applied or tabletting process employed. A simpler way of producing tablets is by direct compressing where tablets are formed directly after the dry mixing of the active drug substance and the additive(s). However, in order to use a dry compression method the crystalline active drug substance must have good flowability and compressibility. This can be achieved by adding one or more further additives but these further additives are often expensive.

An agglomeration technique has been developed in which crystals of an active drug substance can be directly transformed to microgranules during the crystallization process (see for instance J. Pharm. Sci., Vol 42, No 11, November 1985). By using this the flowability and compressibility of the active drug substance are improved and the active drug substance can be directly compressed to form tablets.

Japanese patent application JP58143832 discloses the preparation of spherical crystals of a crystallisable hydrophobic compound (I), comprising the steps of:

i. dissolving (I) in a mixed solvent comprising 7.0–9.0 parts by weight of water, 2–10 parts by weight of water-immiscible solvent(s) (II), and 10–35 parts by weight of a solvent which is miscible with both water and (II); and, ii. agitating the solution.

Japanese patent application JP01279869 discloses the preparation of spherical crystals of certain heterocyclic carboxylic acids. The crystals are prepared by dissolving the heterocyclic carboxylic acid in aqueous ammonia solution and adding a water-immiscible organic solvent and an organic solvent which is miscible with both water and the immiscible organic solvent mixture.

Japanese patent application JP04077422 discloses the preparation of spherical granules of clorprenaline hydrochloride by dissolving clorprenaline hydrochloride in a good solvent, dispersing the solution in a poor solvent and evaporating.

The methods disclosed in these Japanese patent applications require substantial stirring, which would result in difficulties if these methods were scaled up. Further, is addition of an emulsifier is necessary in order to prevent droplets coalescing. These prior art methods are applicable only for fast crystallizing substances.

When these agglomeration techniques are applied to substances having slow crystallization kinetics a paste-like precipitate with unsuitable properties is formed. Also, in large scale production difficulties would be met in obtaining the extremely high stirring rates that would be required with applications based on these techniques.

Document WO 97/49681 discloses a process for isolating crystalline fluvastatin sodium form B which comprises: (a) dissolving fluvastatin sodium in a first organic solvent or a mixture of a first organic solvent and water; (b) adding water if required and a polar precipitating organic solvent so as to obtain crystallization of fluvastatin sodium form B, optionally following seeding with crystalline fluvastatin sodium form B; and (c) isolating and drying the crystalline fluvastatin sodium form B thus obtained. This process results in needlelike crystals of fluvastatin sodium form B.

None of the methods mentioned above are suitable for the production of compact, spherical aggregates with narrow size distribution which would allow subsequent use of a coating process.

DISCLOSURE OF THE INVENTION

A process has now been found by which compact, spherical agglomerates of inogatran with a narrow size distribution (from 30 to 110 $\mu$m, especially from 30 to 100 $\mu$m) can be formed.

The present invention provides a process for producing spherical agglomerates of inogatran (for example inogatran anhydrate) comprising the consecutive steps of:

a) dissolving inogatran in one of its instable, hygroscopic, hydrate forms (for example inogatran monohydrate) in a mixture of a good solvent for inogatran (L1) and a poor solvent for inogatran (L3) to form a concentrated solution, b) optionally filtering the solution, c) concentrating the concentrated solution further, d) adding a non-solvent for inogatran (L2) to obtain supersaturation, and e) adding further (L2) when nucleation has started.

Steps (a) to (e) can be followed by measures to isolate the product.

According to the process of the present invention there is no specific demand for stirring and the process can be easily scaled up. The spherical agglomerates of inogatran produced by the process of this invention require no additives for improving their flowability or compressibility prior to tabletting by a dry compression method.

In the present specification a good solvent is defined as a liquid in which inogatran is very soluble (that is, more than about 0.03 g inogatran/g solvent); a poor solvent is a liquid where inogatran is sparingly to very slightly soluble (that is, about 0.0001–0.03 g inogatran/g solvent); and a non-solvent where inogatran is practically insoluble (that is, less than about 0.0001 g inogatran/g solvent).

In one aspect of the invention the mixture of (L1) and (L3) has a ratio in the range 0.97–0.90:0.03–0.10 (w/w).

In a further aspect of the invention the amount of (L1), (L2) and (L3) per weight of inogatran is in the range from 7 to 15 ml per g inogatran.

In a still further aspect of the invention the ratio of [(L1)+(L3)]:L2) is preferably from 1:1.5 to 1:4 (v/v).

In step (a) a concentrated solution is a solution having, for example, more than 10 g inogatran per 100 ml of solvent (such as more than 20 g inogatran per 100 ml of solvent).

As an optional step between steps (b) and (c) a further step can be added wherein the equipment and the filter plate is washed with (L1) in order to minimize losses of inogatran.

In another aspect of the invention an appropriate amount of inogatran is dissolved in a mixture of L1 and L3 to form a highly concentrated solution. Optionally, the solution is filtered. Non-solvent L2 is then added slowly to the highly concentrated solution while stirring slowly to allow (as visually judged by the first appearance of opalescence) the formation of small quasi-emulsion droplets of inogatran/L1/L3 in the dispersion medium L2. The solution is preferably seeded to start nucleation and, when nucleation has occurred, more L2 is added. The crystallization is then allowed to proceed until equilibrium has occured. Preferably the product obtained is filtered and dried after equilibrium has been achieved.

The size of the spherical agglomerates of inogatran produced by the process is primarily dependent on the size of the quasi-emulsion droplets and stirring has only a marginal effect on the size of the quasi-emulsion droplets.

Any type of solvent can be used in the process of the invention. Suitable solvents for inogatran are: L1=ethanol; L2=ethyl acetate; L3=water, but other choices are possible.

The size of the quasi-emulsion droplets (and thus the size of the agglomerates produced) can be controlled by temperature, drug concentration and volume ratios of liquids used in the process.

Compact, spherical agglomerates of inogatran with a narrow size distribution (30 to 110 $\mu$m) can be obtained by the process according to the invention. An increase of the temperature decreases the size of the agglomerates while a decrease in temperature increases the size of the agglomerates. Also, a higher concentration of inogatran in the L1/L3 mixture (such as the ethanol/water mixture) gives larger agglomerates. If the amount of water is too high, the process tends to give other polymorphs of inogatran which does not meet the requirements of being compact and spherical. Instead soft porous and spherical agglomerates are obtained. Also, too much ethanol gives a variable size distribution. Too much of the ethyl acetate gives agglomerates that stick to the walls of the beaker. Finally, it was found that when the amount of ethyl acetate used in the last addition was too high, an emulsion-like system was formed without giving agglomerates of the desired properties. Therefore, it was quite surprising to find that compact, spherical particles can be obtained with the present invention.

The following Examples illustrate the invention.

EXAMPLE 1

This Example illustrates the preparation of inogatran monohydrate.

[2R-[2S]]-N-[2-[2-[[[3-[(Aminoiminomethyl)amino]propyl]amino]carbonyl]-1-piperidinyl]-1-(cyclohexylmethyl)-2-oxoethyl]-glycine benzyl ester (see WO9311152, 88 kg) was dissolved in ethanol (792 L, 99.5%) at 18° C. Then palladium on carbon (4.4 kg) was added as a slurry in ethanol (99L). After evacuation three times with nitrogen, a total of 10.4 m$^3$ hydrogen was added at an inner temperature of 25° C. The reaction was complete (99.3%) after 4 hours. The catalyst was filtered off and washed with ethanol (82 L) and water (82 L). The solution was then concentrated by evaporation of solvent to a final volume of 200 L. Then, water (330 L) and 1 equivalent of concentrated HCl (12.6 kg) was added. Subsequently, 175 kg solvent was evaporated until the concentration of inogatran in the solution was 21% (w/w). The solution was left overnight after which 0.5 equivalents HCl (6.3 kg) was added to dissolve some crystals. The solution was then heated to 30° C. Thereafter, 105 kg solvent was evaporated. Absolute ethanol (15 L) was added and the solution was then extracted twice with ethyl acetate at 20° C. (118 kg and 100 kg respectively). To the remaining water solution 53 kg ethyl acetate was added. The inner temperature was then adjusted to 25° C. and 1.52 eq. Of NaOH as 20% aqueous solution (41 kg) was added. Then 0.25 kg 50% NaOH was added to adjust pH to 10. The solution was then cooled down to 15° C. in 6 hours. Crystallisation started spontaneously at an inner temperature of 23° C. The slurry was centrifugated and the crystals were washed two times with 50 L water. The crystals were dried under vacuum at 40° C. leaving inogatran monohydrate (49 kg).

EXAMPLE 2

This Example illustrates the preparation of inogatran anhydrate.

Inogatran monohydrate (Example 1, 49 kg) and 4.6 L water were added to absolute ethanol (260 L) at 18° C. The resulting solution was clear filtrated and the filter was washed with 50 L absolute ethanol. The solution was then concentrated by evaporation until the volume was 100 L. Then, ethanol (15 kg) and water (6.7 kg) were added, the solution then heated to 40° C. and, finally, ethyl acetate (330 kg) was added over a period of 3 hours. Crystallisation started spontaneously when approximately 300 kg ethyl acetate had been added. The slurry was left at 40° C. overnight (11 h). The slurry was then centrifugated, washed twice with 50 L of a mixture of ethyl acetate and ethanol (4:1). The resulting crystals were dried at 40° C. to leave inogatran anhydrate (46 kg).

EXAMPLE 3

This Example illustrates the preparation of inogatran anhydrate.

Inogatran (monohydrate; 5.5% of water; 26.6 kg) was dissolved in 140 L of ethanol (99.5%) and 1.13 L of water at 30° C. The solution was filtered to obtain a clear solution and was washed with 20 L of ethanol. The solution was concentrated by evaporation of about 105 L of ethanol under reduced pressure and the temperature was adjusted to 25° C. To this solution was added 90 L of ethyl acetate over 20 minutes and the resulting mixture was seeded with inogatran anhydrate (3–5 g). Nucleation appeared after about 1 hour and after visually judging the appearance of opalescence further 80 L of ethyl acetate was added. The system was left over night for equilibrium to occur. The product was centrifugated, washed with a mixture of 12 L ethanol and 47 L of ethyl acetate and was dried at 40° C. and vacuum. Filtration provided inogatran anhydrate (24.05 kg; yield 96%, purity (HPLC) 99.8%) as compact, spherical agglomerates having a narrow size distribution and a medium particle size 103 $\mu$m (Malvern).

EXAMPLE 4

This Example illustrates the recrystallisation of inogatran anhydrate.

Inogatran (anhydrate) was dissolved in ethanol:water (90:10% w/w) (concentration 5–6 ml/g of inogatran) at reflux (about 78° C.) and the resulting solution was cooled to room temperature. The system was filtered to obtain a clear solution and was concentrated by azeotropic evaporation of ethanol/water (96/4% w/w) to a volume of 2.5–3 ml/g of inogatran. The resulting solution was analysed for amount of water by the Karl Fischer method. If the amount of water was higher than 0.2 g water/g of inogatran then 3–5 ml ethanol (99.5%)/g of inogatran was added and the evaporation was repeated until the amount of water was in the range 0.1–0.2 g water/g of inogatran.

The temperature of the solution was adjusted to 20–40° C., ethyl acetate (3.5–4 ml/g of inogatran) was added, nucleation occurred after about 1 hour and further ethyl acetate (2.5–4 ml/g of inogatran) was added. The system was left for at least 3 hours to reach equilibrium and product was then filtered off and dried.

What is claimed is:

1. A process for producing spherical agglomerates of inogatran comprising the consecutive steps of:
    a) dissolving an unstable, hygroscopic, hydrate form of inogatran in a mixture of a good solvent for inogatran and a poor solvent for inogatran to form a concentrated solution;
    b) optionally filtering the solution;
    c) concentrating the concentrated solution further by evaporation;
    d) adding a non-solvent for inogatran to the concentrated solution until the solution becomes supersaturated; and
    e) adding additional non-solvent when nucleation has started to produce a product comprising spherical agglomerates of inogatran,
       wherein the solubility of inogatran in the good solvent is more than about 0.03 g inogatran/g solvent,
       the solubility of inogatran in the poor solvent is about 0.0001–0.03 g inogatran/g solvent, and
       the solubility of inogatran in the non-solvent is less than about 0.0001 g inogatran/g solvent.

2. The process according to claim 1, wherein the ratio of the good solvent to the poor solvent in the solution is in the range of 0.97–0.90:0.03–0.10 (w/w).

3. The process according to claim 1, wherein the amount of the good solvent, the non-solvent, and the poor solvent per weight of inogatran is in die range of from 7 to 15 ml per g inogatran.

4. The process according to claim 1, wherein the ratio of [(good solvent)+(poor solvent)]:(non-solvent) is from 1:1.5 to 1:4 (v/v).

5. The process according to claim 1, wherein the concentrated solution in step a) has more than 10 g inogatran dissolved per 100 ml of solvent.

6. The process according to any one of claims 1–5, wherein the good solvent is ethanol.

7. The process according to any one of claims 1–5, wherein the non-solvent is ethyl acetate.

8. The process according to any one of claims 1–5, wherein the poor solvent is water.

9. The process according to claim 1, wherein the concentrated solution in step a) has more than 20 g inogatran dissolved per 100 ml solvent.

10. The process according to any one of claims 1–5, wherein the good solvent is ethanol the non-solvent is ethyl acetate, and the poor solvent is water.

* * * * *